United States Patent [19]
Kennedy et al.

[11] Patent Number: 5,242,983
[45] Date of Patent: Sep. 7, 1993

[54] POLYISOBUTYLENE TOUGHENED POLY(METHYL METHACRYLATE)

[75] Inventors: Joseph P. Kennedy; Gretchen C. Richard; Michael J. Askew, all of Akron, Ohio

[73] Assignee: Edison Polymer Innovation Corporation

[21] Appl. No.: 854,421

[22] Filed: Mar. 19, 1992

[51] Int. Cl.$^5$ .................. C08F 255/10; C08L 33/12; A61F 2/28
[52] U.S. Cl. ..................... 525/309; 525/227; 525/319; 525/903; 526/329; 526/348.7; 623/16
[58] Field of Search .............. 525/227, 309, 319, 903; 526/329, 348.7

[56] References Cited

U.S. PATENT DOCUMENTS

| | | | |
|---|---|---|---|
| 3,944,631 | 3/1976 | Yu et al. | 260/881 |
| 4,085,168 | 4/1978 | Milkovich et al. | 260/886 |
| 4,123,409 | 10/1978 | Kaelble | 260/29.1 SB |
| 4,276,394 | 6/1981 | Kennedy et al. | 525/245 |
| 4,287,317 | 9/1981 | Kitagawa et al. | 525/309 |
| 4,316,973 | 2/1982 | Kennedy | 525/335 |
| 4,442,261 | 4/1984 | Kennedy et al. | 525/324 |
| 4,486,572 | 12/1984 | Kennedy | 525/283 |
| 4,524,188 | 6/1985 | Kennedy et al. | 525/333.7 |
| 4,711,913 | 12/1987 | Tateosian et al. | 522/14 |
| 4,829,127 | 5/1989 | Muramoto et al. | 525/902 |
| 4,837,279 | 6/1989 | Arroyo | 525/193 |
| 4,863,977 | 9/1989 | Tateosian et al. | 522/14 |
| 4,942,204 | 7/1990 | Kennedy | 525/293 |
| 4,994,523 | 2/1991 | Sasaki et al. | 525/63 |
| 5,066,730 | 11/1991 | Kennedy et al. | 525/319 |

OTHER PUBLICATIONS

"Living Carbocationic Polymerization. IV. Living Polymerization of Isobutylene", R. Faust et al., *Journal of Polymer Science: Part A: Polymer Chemistry*, vol. 25, 1847–1869 (1987).

"Living Carbocationic Polymerization XIV. Living Polymerization of Isobutylene with Ester. TiCl$_4$ Complexes", G. Kaszas et al., *Makromolecular Chem., Macromol. Symp.*, 13/14, 473–493 (1988).

"New Telechelic Polymers and Sequential Copolymers by Polyfunctional Initiator-Transfer Agents (Inifers) V. Synthesis of α-tert-Butyl-ωisopropenylpolyisobutylene and α,ω-Di(isopropenyl)polyisobutylene", J. Kennedy et al., *Polymer Bulletin*, 1, 575–580 (1979).

"New Telechelic Polymers and Sequential Copolymers by Polyfunctional Initiator-Transfer Agents (Inifers). VII. Synthesis and Characterization of α,ω-Di(hydroxy)polyisobutylene", B. Ivan et al., *Journal of Polymer Science: Polymer Chemistry Edition*, vol. 18, 3177–3191 (1980).

"Macromers by Carbocationic Polymerization. IV. Synthesis and Characterization of Polyisobutenyl Methacrylate Macromer and Its Homopolymerization and Copolymerization with Methyl Methacrylate", J. Kennedy et al., *Journal of Polymer Science: Polymer Chemistry Edition*, vol. 21, 1033–1044 (1983).

"Living Carbocationic Polymerization IX. Three-Arm Star Telechelic Polyisobutylenes by C$_6$H$_3$(C(CH$_3$)$_2$OCH$_3$)$_3$/BCl$_3$ Complexes", M. Mishra et al., *Polymer Bulletin*, 17, 307–314 (1987).

*Primary Examiner*—Vasu S. Jagannathan
*Attorney, Agent, or Firm*—Louis J. Weisz

[57] ABSTRACT

A bone cement is prepared by synthesizing a polymeric composition comprising poly(methyl methacrylate) cross-linked by copolymerization with tris(ω-methacryloyl) polyisobutylene. A powder is formed from the composition, and the final cement is prepared by mixing the powder with additional methyl methacrylate in the presence of a catalyst to form a dough-like material that is polymerized in situ to yield a cement useful for orthopedic purposes. Preferred embodiments employ tris(ω-methacryloyl) compounds within a particular molecular weight range, and which are present in the powder in particular amounts relative to the poly(methyl methacrylate) component therein.

5 Claims, 4 Drawing Sheets

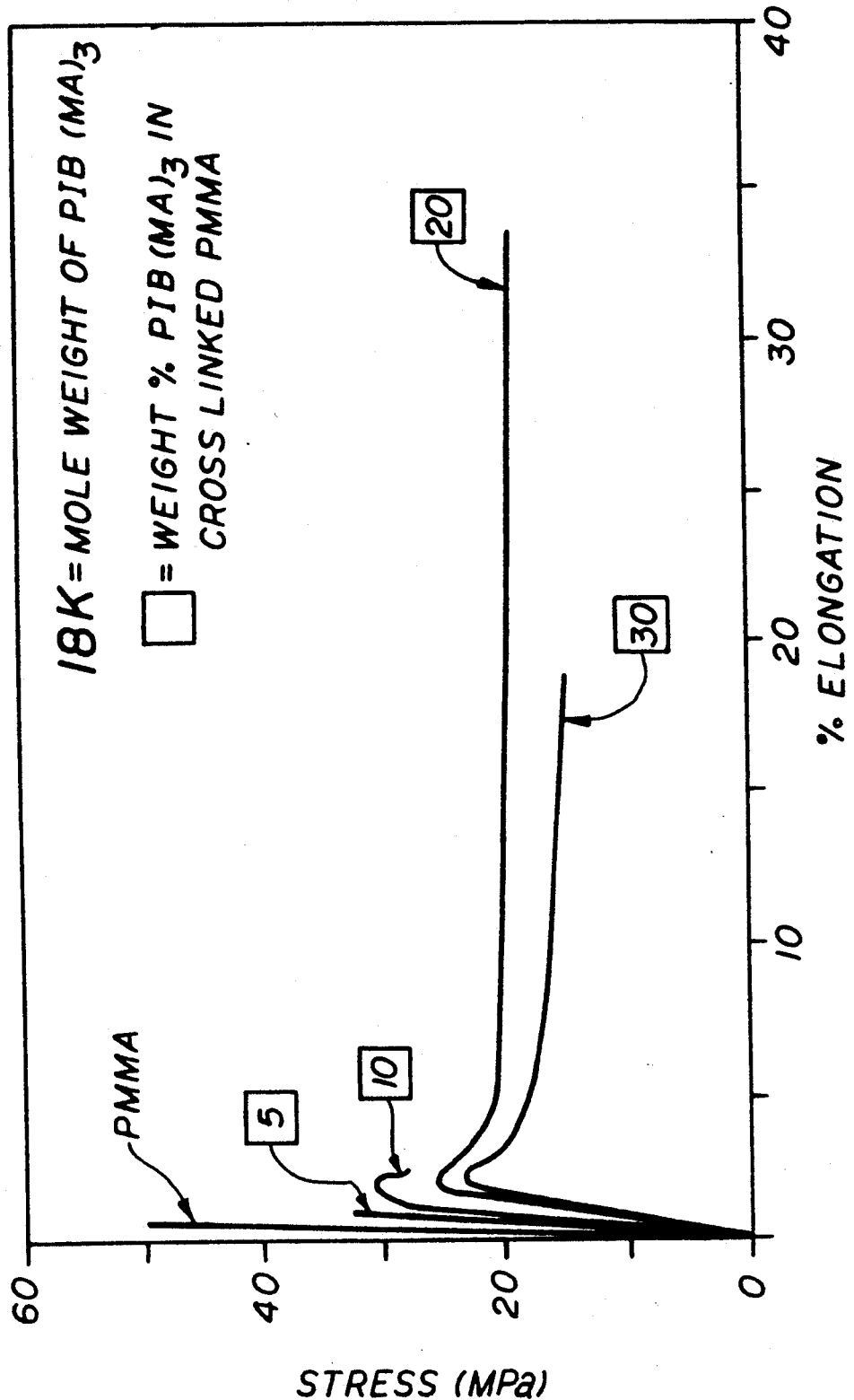

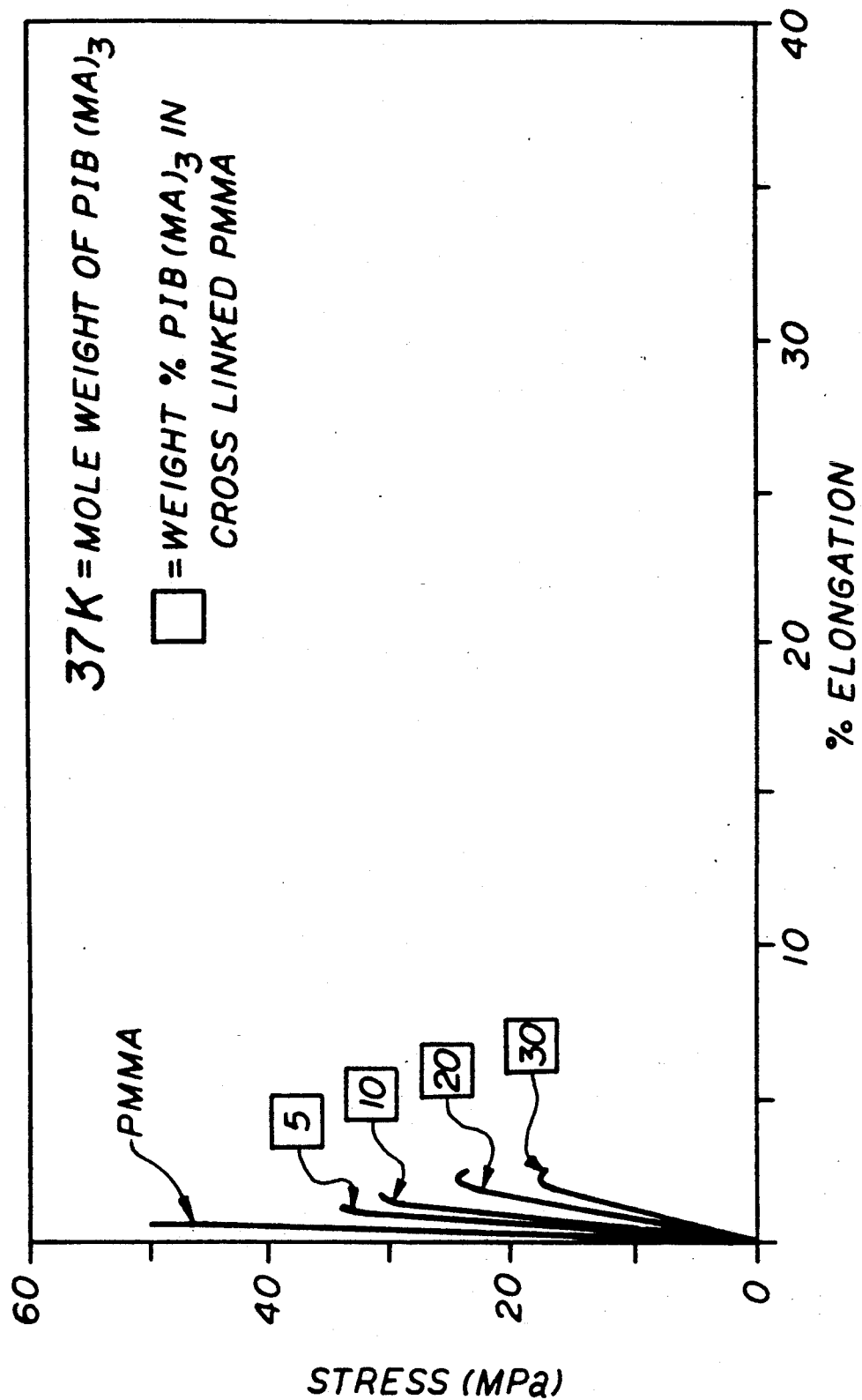

5,242,983

POLYISOBUTYLENE TOUGHENED POLY(METHYL METHACRYLATE)

TECHNICAL FIELD

This invention relates to cements formed by semi-simultaneous interpenetrating networks of synthetic polymers. More particularly, this invention relates to cements comprising poly(methyl methacrylate) compositions toughened by their interaction with poly(methyl methacrylate) cross-linked by methacrylate-capped tritelechelic polyisobutylene compounds. Specifically this invention relates to improved bone cements prepared by polymerizing methyl methacrylate in the presence of additional poly(methyl methacrylate) previously and partially cross-linked with methacrylate-capped tritelechelic polyisobutylene, thereby forming polymeric compositions of superior toughness, which also display excellent ultimate flexural strength and stiffness compared to the polyacrylate bone cements presently in use.

BACKGROUND OF THE INVENTION

Bone cements are widely used in orthopedic surgery, for example, for the replacement of hip joints, in craniofacial reconstruction procedures, in dentistry and in similar applications. In the past, such cements have commonly taken the form of polyacrylate compositions polymerized in situ, for instance, to anchor bone prostheses in place. Typically, such systems include two interreactive components, one a powder comprised of poly(methyl methacrylate), PMMA, and the other, liquid methyl methacrylate, MMA. The two components are intermixed to form a kneadable dough which is introduced, for example in the case of a hip replacement, into a prepared cavity in a femur, the metal alloy prosthesis being inserted into the cavity thereafter. The "dough" can be manipulated by the physician for a period of about seven minutes, at which time, it will have polymerized to a viscosity such that it becomes impossible to manipulate it further. A bone prosthesis thus installed is not only firmly set in position, but the bone cement used to embed it acts to distribute stresses operative at the prosthesis-cement interface over a wide area, thereby reducing stress concentrations to a manageable level.

Unfortunately, while bone cements of the type described are characterized by a high degree of strength, they also display certain disadvantageous characteristics which the invention is designed to overcome. For instance, one difficulty frequently encountered with poly(methyl methacrylate) bone cements of the prior art resides in the fact that while poly(methyl methacrylate) exhibits high strength, the polymer is relatively brittle. Consequently, prosthesis implants so fastened tend over time to become loosened due to the stresses constantly being experienced. Loosening is a major cause of failures of this type of reconstruction.

In addition, however, the constant wear and tear to which such implants are exposed tends to result in erosion of the brittle polymer, accompanied by the concurrent formation of small wear particles. Eventually, therefore, the anchoring interfaces become weakened and insufficient to function properly, leading to ultimate failure of joints so established. In this regard, currently available data indicates that remedial work necessitated as a consequence of joint replacement failures may be required in as many as about 4.5% of such cases.

In view of the preceding, therefore, it is a first aspect of this invention to provide a superior bone cement composition for use in medical procedures.

It is a second aspect of this invention to provide bone cement compositions that are tougher than the polyacrylate compositions presently in use.

Another aspect of this invention is to provide bone cements that avoid the brittleness and concomitant inferior fatigue characteristics that are associated with poly(methyl methacrylate) compositions of the prior art.

Yet another aspect of this invention is to provide novel three-arm, or star polyisobutylene compositions comprising methacrylate tritelechelic polyisobutylenes.

An additional aspect of this invention is to provide a poly(methyl methacrylate) polymer toughened by having been cross-linked with methacryloyl-capped, three-arm polyisobutylene compositions.

A further aspect of this invention is to provide a new type of semi-simultaneous interpenetrating network useful in preparing toughened bone cements.

The preceding and additional aspects of this invention are provided by a polymeric composition consisting essentially of tris(ω-methacryloyl) polyisobutylene.

The preceding and other aspects of the invention are provided by a composition comprising poly(methyl methacrylate) partially cross-linked with a telechelic compound consisting of tris(ω-acryloyl) polyisobutylene.

The preceding and further aspects of the invention are provided by a bone cement comprising the reaction product of (1) a polymeric composition according to the preceding paragraph in which the telechelic compound is tris(ω-methacryloyl) polyisobutylene, and (2) methyl methacrylate.

The preceding and yet additional aspects of the invention are provided by a process for making compositions of the type described in the penultimate paragraph in which the tris(ω-methacryloyl) polyisobutylene and the methyl methacrylate are agitated until a gelled reaction product begins to form, and then reacted further without agitation until a solid polymeric product is formed.

The preceding and still further aspects of the invention are provided by a semi-simultaneous interpenetrating network of a polymeric composition comprising poly(methyl methacrylate) cross-linked with tris(ω-methacryloyl) polyisobutylene, the polymeric composition being interpenetrated with a poly(methyl methacrylate) homopolymer.

BRIEF DESCRIPTION OF THE FIGURES

The invention will be better understood when reference is had to the following figures in which:

FIGS. 2A–2C show stress-strain curves of poly(methyl methacrylate) compositions cross-linked with the tris(ω-methacryloyl polyisobutylenes of the invention.

DETAILED DESCRIPTION OF THE INVENTION

Figure 1:
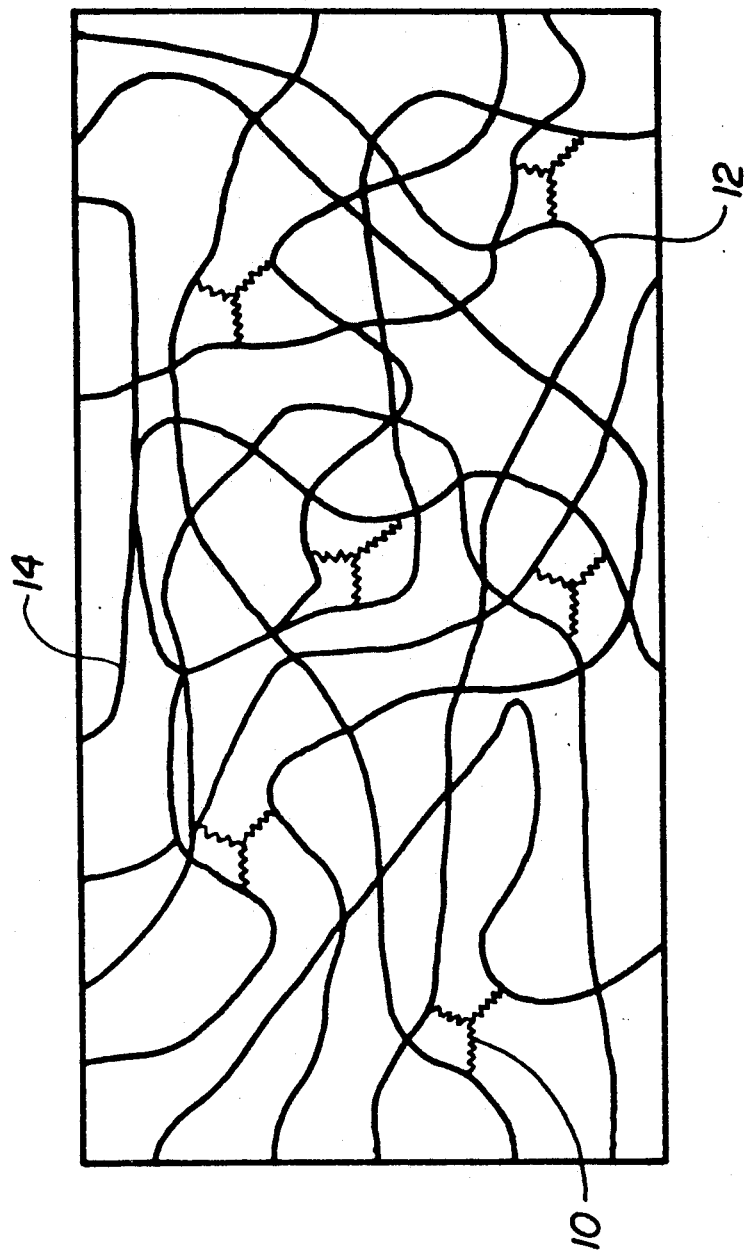
FIG. 1 is a semi-simultaneous interpenetrating network of (1) methyl methacrylate homopolymer, and (2) poly(methyl methacrylate) cross-linked with tris(ω-methacryloyl) polyisobutylene.

The invention disclosed in the following achieves the "toughening" of otherwise brittle poly(methyl methacrylate) plastic compositions by the reaction therewith of an elastomeric component, e.g., tris(ω-methacryloyl) isobutylene. In order to achieve its objective of toughening the compositions, the glass transition temperature, Tg, of an elastomer must be below the temperature at which the matrix into which it is to be introduced is to be used. Further, the elastomer must be immiscible with the matrix in order to allow dispersion within the brittle matrix to yield an appropriate morphology. In addition, the interfacial adhesion between the elastomer and the matrix must be strong enough to achieve adequate energy dissipation. The microdomain morphology must also be preserved, i.e., the elastomer domains must be substantially uniformly dispersed throughout the matrix and must remain dispersed.

The above objectives are attained according to the disclosed invention through the initial preparation of a three-arm, star polyisobutylene compound, each of the three arms being capped with an acryloyl group capable of reacting with methyl methacrylate. Since control of molecular weight is important in providing the results hereinafter described, the star polyisobutylene compound is formed with end group functionality on the polyisobutylene arms thereof by means of telechelic, living polymerizations.

Following preparation of the acryloyl tritelechelic polyisobutylene, sometimes referred to herein as tris(ω-methacryloyl) polyisobutylene, or PIB (MA)₃, the polyisobutylene is copolymerized with methyl methacrylate to form one of the components employed in the bone cement. Since the tritelechelic polyisobutylene does not dissolve in methyl methacrylate to any significant degree, a mutual solvent is employed to prepare the reaction mixture. The solid copolymer thus formed is made available in the form of a powdered component for mixing and polymerizing with still further methyl methacrylate to produce the final bone cement. The reaction of the acryloyl tritelechelic polyisobutylene with the methacrylate to form a cross-linked and toughened copolymer proceeds according to the following equation:

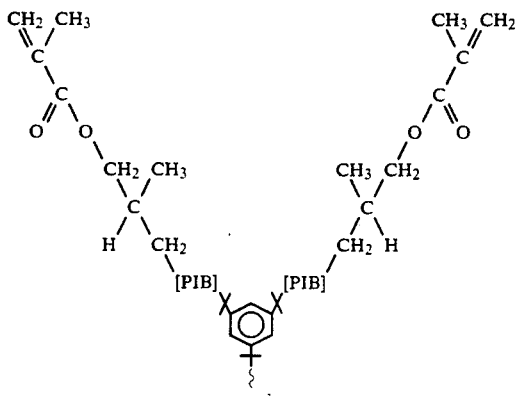

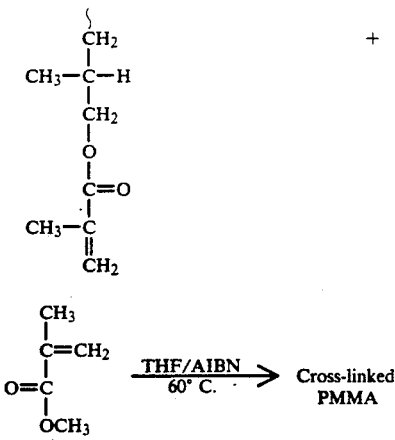

In the reaction shown, the tritelechelic polyisobutylene methacryloyl end group is of comparable reactivity with the methyl methacrylate to which it is covalently bound during the reaction. The three arms of the telechelic polyisobutylene are freely accessible to the methyl methacrylate, and the resulting reaction yields both the cross-linked copolymer of methyl methacrylate with tris(ω-methacryloyl) polyisobutylene, and a methyl methacrylate homopolymer. The two polymers are intertwined and, since they are formed concurrently, constitute a semi-simultaneous interpenetrating network (semi-SIN). The interpenetrating networks of the invention differ from semi-SIN networks previously known in that one of the reactants, i.e., the methyl methacrylate is involved in both reactions, that is, formation of the copolymer, as well as the homopolymer. Selective extraction with acetone and hexane shows the existence of the interpenetrating network described, such network also being confirmed by the presence of two glass transition temperatures, determined through employment of differential scanning calorimetry and dynamic mechanical thermal analysis.

FIG. 1 illustrates a schematic, semi-simultaneous interpenetrating network of the type contemplated by the invention. The Figure shows the methacryloyl telechelic polyisobutylene 10, serving to cross-link the methyl methacrylate polymers 12. The methyl methacrylate homopolymers 14 are also to be seen, intertwined with the cross-linked poly(methyl methacrylate) molecules.

The presence of the rubber portion in the acryloyl telechelic polyisobutylenes provides a mechanism which allows energy-dissipation in the form of crazing and shear yielding to occur, thereby providing the toughening effect achieved. To provide such results, however, and as previously indicated, it is necessary that the acryloyl telechelic polyisobutylenes be uniformly distributed throughout the reaction mixture during formation of the copolymer, and that the uniform microdomain morphology be preserved. In order to assure this, it has been found desirable to conduct the reaction in two steps. During the first of these, the acryloyl telechelic polyisobutylene and the methyl methacrylate are combined in a solvent and stirred during an initial polymerization until the reaction mixture begins to gel; at such point the reacting components have become immobilized. Thereafter, in a second step, stirring can be discontinued and polymerization continued to provide the desired solid product. When thus formed, the interpenetrating networks provide good interfacial strengths as between the tris($\omega$-methacryloyl)-polyisobutylene and the poly(methyl methacrylate), due to the uniformly distributed PIB—(MA)$_3$, and to the three points of attachment to the poly(methyl methacrylate) matrix provided by the three reactive arms.

With respect to the preparation of the cross-linked PMMAs of the invention, and as will be shown in the following in connection with the discussion of physical properties, it has been found that the molecular weight of the methacryloyl telechelic polyisobutylenes should be controlled within particular limits if optimal physical properties of the cross-linked copolymer are to be realized. As might be expected, as the molecular weight increases, providing longer polyisobutylene chains, toughness of the cross-linked poly(methyl methacrylate) increases. Surprisingly, however, it has been found that when the molecular weight increases beyond a certain point, inferior products with decreased toughness are produced. In regard to the foregoing, it has been determined that the molecular weight of the acryloyl telechelic polyisobutylenes should be controlled between about 6,000 to about 25,000 grams per gram mole, and a control range of from about 15,000 to about 20,000 grams per gram mole has been found to provide superior results.

In addition, and in order to realize the benefits of molecular weights controlled within the range shown, it is necessary that the molecular weight distribution of the acryloyl telechelic polyisoibutylene, be maintained within a uniform range. In this regard, it has been found, for example, that the ratio of weight average molecular weight to number average molecular weight, $M_w/M_n$, of such compounds have a maximum value of about 1.5. In a preferred embodiment, the molecular weight distribution will, however, be maintained so that such ratio comprises a value no greater than between about 1.2 to about 1.3.

In carrying out the copolymerization, resort will be had to an initiator/catalyst, for example, AIBN, azobisisobutyronitrile, although other catalysts of the types well known in the art may also be employed. Typically, about 0.3 to about 0.7 mole percent of the initiator, based on the moles of methacrylate functional groups in the reaction mixture will be employed. The amount of initiator present will determine the molecular weight of poly(methyl methacrylate) in the cross-linked copolymer, and therefore, the mechanical properties of the same. The temperature of the polymerization, which affects the rate of decomposition of the AIBN and the mobility of the reactants, however, can also be used to adjust the character of the poly(methyl methacrylate) matrix, and therefore, the physical properties of the cross-linked copolymer.

As mentioned in the preceding, the acryloyl telechelic polyisobutylene is not soluble in methyl methacrylate; consequently, both must be dissolved in a mutual solvent in order to achieve the desired reaction. While tetrahydrofuran, THF, has been found to be admirably suited for the purpose since it has a desirably low boiling point and presents minimal processing and ecological problems, any solvent capable of dissolving both components is satisfactory for the purposes of the invention.

As in the case of the molecular weight of the acryloyl telechelic polyisobutylenes, it has also been found that the amount of such material in the cross-linked copolymer affects the physical properties of the copolymer. In this regard, it has been determined to be desirable to provide compositions in which the concentration of acryloyl telechelic polyisobutylene constitutes from about 5 to about 30 weight percent of the cross-linked copolymer. However, a more preferable range has been found to be from about 15 to about 20 weight percent. In general, the lower the amount of the acryloyl telechelic polyisobutylene present, the easier it is to mix the copolymer with still further methyl methacrylate in preparing the final bone cement.

The effects of molecular weight and of concentration on physical properties discussed above are confirmed in TABLE 1 below, in which the first number in the sample indicates the molecular weight of the acryloyl telechelic polyisobutylene, for example, 6K represents such a compound having a molecular weight of 6000 g/mole. The last number indicates the concentration (wt %) of the acryloyl telechelic polyisobutylene in the cross-linked poly(methyl methacrylate) copolymer.

TABLE 1

| | Uniaxial Tensile Test | | | | |
|---|---|---|---|---|---|
| Sample | E (1%) (MPa) | $\sigma_y$ (MPa) | $\sigma_b$ (MPa) | $\epsilon_b$ (%) | U (J/M$^3$) × 10$^{-6}$ |
| 6K5 | 3390 ± 66 | 38.4 ± 0.8 | 32.9 ± 4.0 | 6.4 ± 4.7 | 2.15 ± 1.58 |
| 6K10 | 3080 ± 320 | 37.8 ± 0.3 | 30.0 ± 4.3 | 8.0 ± 3.0 | 2.65 ± 0.96 |
| 6K20 | 970 ± 49 | 23.6 ± 0.8 | 14.2 ± 0.1 | 20.1 ± 3.4 | 4.11 ± 0.75 |
| 6K30 | 1530 ± 186 | 22.6 ± 0.6 | 18.7 ± 4.6 | 5.0 ± 1.4 | 0.94 ± 0.30 |
| 18K5 | 3040 | 32.3 ± 0.2 | 32.2 ± 0.2 | 0.8 ± 0.1 | 0.202 ± 0.014 |
| 18K0 | 2880 ± 62 | 31.2 ± 0.3 | 28.8 ± 0.6 | 1.8 ± 0.8 | 0.485 ± 0.185 |
| 18K20 | 2450 ± 20 | 24.7 ± 0.1 | 18.4 ± 0.3 | 32.9 ± 9.5 | 6.76 ± 1.85 |
| 18K30 | 1660 ± 57 | 23.7 ± 0.3 | 16.7 ± 1.2 | 18.2 ± 1.7 | 3.61 ± 0.344 |
| 37K5 | 3240 ± 210 | 34.3 ± 1.8 | 34.3 ± 1.8 | 1.1 ± 0.5 | 0.340 ± 0.020 |
| 37K10 | 3000 ± 100 | 32.0 ± 0.5 | 31.9 ± 0.5 | 1.3 ± 0.5 | 0.347 ± 0.150 |
| 37K20 | 2220 ± 170 | 25.7 ± 0.2 | 25.1 ± 0.7 | 2.2 ± 0.1 | 0.489 ± 0.009 |
| 37K30 | 1770 ± 80 | 19.2 ± 0.4 | 19.0 ± 0.3 | 2.1 ± 0.4 | 0.362 ± 0.020 |

The data shown in TABLE 1 reflects uniaxial tensile testing conducted on an Instron Tensile Tester, employing an extensometer for elongation measurement. The gauge length used is 2.54 centimeters, and the strain rate is 1.27 centimeters/minute. Relative toughness is calculated as "work of rupture", U, i.e., the area under the stress/strain curve in Joules/M$^3$, using the cut-and-weigh method.

Figure 2A:
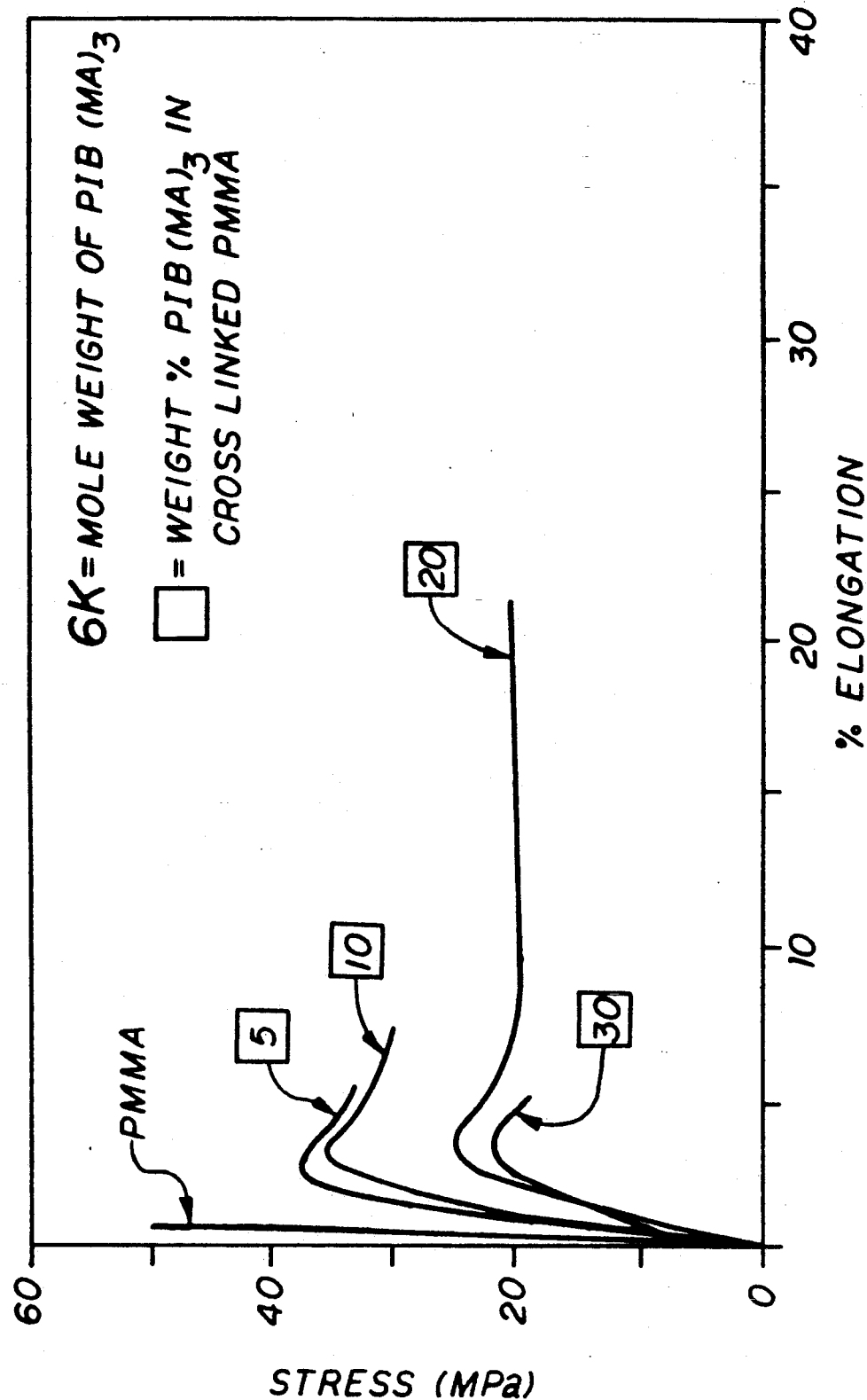

TABLE 1 shows the average results obtained for Young's modulus at 1% elongation, E(1%); yield strength ($\sigma_y$); ultimate breaking strength ($\sigma_b$); elongation at break $\epsilon_b$ and work of rupture (U). Representative curves are plotted in FIGS. 2A-2C, from which it can be seen that the toughest copolymer had a molecular weight of 18,000, and contained about 20% of the methacryloyl telechelic polyisobutylene. All of the samples of the invention plotted in FIGS. 2A–2C show greater toughness than a commercial poly(methyl methacrylate) composition, included as a standard for comparison.

While not wishing to be bound by the theory, it is apparent that even 5 weight percent of the methacryloyl telechelic polyisobutylene is sufficient to result in an increase in toughness. However, apparently at some point exceeding a concentration of 20% of the acryloyl telechelic polyisobutylene, the most effective toughening of the cross-linked material has been crossed. The decrease in tensile properties suggests that this may happen when a semi-continuous acryloyl telechelic polyisobutylene phase exists, i.e., where the rubbery domains are interconnected. Such a morphology would probably not result in effective rubber roughening.

The final bone cement is prepared by mixing the cross-linked copolymer with additional methyl methacrylate. The copolymer is reduced to the form of a powder, while the methyl methacrylate is a liquid, the two being mixed and kneaded together immediately prior to use. Polymerization, which occurs thereafter due to the inclusion of a polymerization catalyst in the powdered copolymer, results in a hard, tough material which is admirably suited, for example, to fastening a prosthesis to a bone Mixing of the powder with the liquid component normally can be accomplished in from about 45 seconds to about 2 minutes, mixing being continued until the composition can be readily handled and manipulated into the areas where it is required. The ratio of powder to liquid required to produce a workable "dough" will depend upon a variety of factors, including the particle size of the powdered, cross-linked copolymer, as well as the amount of acryloyl telechelic polyisobutylene contained therein. Optimum ratios in a given system are readily determined by experimentation; however, it has been found that powder-to-liquid ratios from about 1.3/1 to about 2/1 normally provide satisfactory results.

TABLE 2 sets forth a typical composition for both a commercial bone cement, as well as a bone cement employing the cross-linked copolymers of the invention. In the formulation, the N,N-dimethyl-p-toluidine functions as an accelerator, while the hydroquinone serves as a stabilizer. The polymerization catalyst employed is benzoyl peroxide (BPO).

TABLE 2

| LIQUID | | POWDER | |
|---|---|---|---|
| Commercial Bone Cement | | | |
| methyl methacrylate | 97.25% | PMMA | 89.25% |
| N,N-dimethyl-p-toluidine | 2.75% | Barium sulfate | 10.0% |
| hydroquinone | 75 ppm | BPO | 0.75% |
| Toughened Bone Cement | | | |
| SAME AS ABOVE | | PMMA | 70.0% 85.0% |
| | | Telechelic PIB | 30.0% 15.0% |
| | | BPO | 0.75% 0.75% |

TABLE 3 shows a series of bone cement formulations which were prepared and tested, and which used different powder/liquid ratios. As a control, one of the cements comprised only poly(methyl methacrylate). The samples thus prepared were mixed with a spatula in an open container, employing a clockwise-counterclockwise mixing cycle, at the rate of 30 cycles/minute. The commercial poly(methyl methacrylate) cement was mixed for 40 seconds, while the mixing time of the experimental cross-linked copolymer with methyl methacrylate varied from 40 seconds to 1.5 minutes. The resulting dough was placed in a 75 mm×90 mm mold recess in a 3.5 mm thick Teflon plate. After one hour, the molded sample was removed and cut into strips 10 mm×75 mm, 3.5 mm thick.

TABLE 3

| Bone Cement Formulation and Final Compositions | | |
|---|---|---|
| POWDER (40 g) | P/L (Powder/Liquid) | BONE CEMENT FINAL COMPOSITION |
| PMMA* | 2/1 | PMMA |
| 18K15 | 1.33/1 | 18K8.5 |
| 18K15 | 1.6/1 | 18K9.2 |
| 18K30 | 1/1 | 18K15 |
| 18K30 | 1.33/1 | 18K17.1 |

*Zimmer commercial product

Flexural testing was conducted according to ISO standard test ISO 5833/1 (Proposed Revision 1986). Bending tests of the bone cement samples were carried out in a water bath at 37° C. on a materials testing machine (Model 812, MTS Systems, Inc., Minneapolis, Minn.) at a support displacement rate of 15 mm/minute. The bending load, measured by the load cell of the materials testing system, and the mid-span deflection, measured by a linear variable displacement transducer (LVDT, Model 7307-X2-AO, Pickering and Co.), were recorded on an X-Y plotter. The bending modulus and bending strength were calculated according to the methods of the ISO test. Compared to the standard poly(methyl methacrylate), it will be seen that the sample containing 9.2% methacryloyl telechelic polyisobutylene displayed significantly improved flexural strength at break, and showed much greater maximum deflection at break. The flexural modulus of the sample also compares very favorably with that of the standard poly(methyl methacrylate) examined.

TABLE 4

| Four Point Bend Results | | | | |
|---|---|---|---|---|
| Telechelic PIB Content* (wt %) | E (MPa) | $\sigma_b$ (MPa) | $\Delta d$ (mm) | Mixing Time |
| 0.0** | 2190 ± 150 | 53.4 ± 4.2 | 4.90 ± 0.16 | 45 sec. |
| 8.5 | 1680 ± 240 | 41.4 ± 6.2 | 5.10 ± 0.04 | 45 sec. |
| 9.2 | 1980 ± 100 | 57.0 ± 2.3 | 6.40 ± 0.87 | 1.5 min. |
| 15.0 | 970 ± 180 | 21.2 ± 5.1 | 4.80 ± 0.60 | 45 sec. |
| 17.0 | 1260 ± 140 | 26.7 ± 7.2 | 3.80 ± 1.30 | 1.5 min. |

*18,000 g/mole
**commercial product
E-flexural modulus
$\sigma_b$-flexural strength at break
$\Delta d$-maximum deflection before break The following example is provided by way of illustration rather than limitation:

EXAMPLE

Synthesis of Initiator

Preparation of 1,3,5-tris(2-methoxy-2-propyl) benzene (tricumyl methyl ether, TCME)

To a $N_2$-flushed, three-liter flask fitted with a condenser, $N_2$ inlet, dropping funnel and magnetic stir bar were added 196 mL (0.588 mole) methylmagnesium bromide (3.0M in diethyl ether) by a syringe. A dilute (ca. 1%) THF solution of 22 g (0.107 mole) 1,3,5-triacetylbenzene was then added dropwise, and addition was continued at a rate that would effect a mild reflux of the diethyl ether. The resulting thick, beige suspension was stirred overnight. The flask contents were cautiously poured into a stirred ice/salt bath (600 q ice/30 g ammonium chloride) and stirred for one hour. The mixture was extracted five times with diethyl ether, and the combined extracts dried over anhydrous magnesium sulfate overnight. After removal of nearly all solvent, the impure, ether-wet product was slurried with toluene for several hours. This caused the product to precipitate as white, rather fine solids. Recrystallization from ethyl acetate at room temperature afforded a 75% yield (16.5 g) of 1,3,5-tris(2-hydroxy-2-propyl)benzene in the form of white needles, m.p. 148°-150° C.

Conversion of the product to the methyl ether (TCME) was accomplished in a round bottom flask, in which 6 g (0.024 mole) of triol were dissolved in 100 mL methanol. To this solution was added a catalytic amount (0.005 mL) of concentrated sulfuric acid, and the system was refluxed for 20 hours. The final clear, light yellow solution was cooled, 100 mL pentane were added, and the mixture was stirred for 30 minutes. The resulting off-white suspension was washed with five portions of distilled water, and the combined organic extracts were dried over magnesium sulfate overnight. The combined, dried organic extracts were then filtered and the solvent evaporated. The crude product was recrystallized at room temperature from petroleum ether. The procedure afforded 5 g (0.017 mole, 70%) of white needles, m.p. 44° C.

Polymerization of Isobutylene (IB)

Polymerizations were conducted in a stainless steel dry box under a dry nitrogen atmosphere in round-bottom flasks. Cooling was achieved by passing liquid $N_2$ through copper coils immersed in a n-heptane bath. The dry box was conditioned by flushing it with dry $N_2$ for several hours.

Isobutylene polymerizations conducted on a 150-200 g scale required a five liter flask to allow the monomer concentration to be below 10% by volume. Monomer was added in three increments, the first portion being added before the $TiCl_4$ or $BCl_3$ solution was added to the flask. The remaining two portions of IB were added at equally timed intervals. N,N-dimethylacetamide (DMA) was used as the electron donor, being placed in the flask before the coinitiator solution was added. The molar amount of DMA was equal to the functional group concentration of the TCME initiator. The TCME/$BCl_3$ and TCME/$TiCl_4$ mole ratios were ⅛ and 1/16, respectively.

Synthesis of 6K PIB—$Cl'_3$

The reaction was conducted in a stainless steel dry box at −40° C. To a 5-liter round-bottom flask were added 8.224 g (0.027 mole) TCME, 2 L precooled methyl chloride (MeCl), 6.4 mL (0.069 mole) DMA, and 74.3 mL (0.904 mole) IB. To initiate the polymerization, a precooled solution of 20.12 mL (25.31 g, 0.216 mole) $BCl_3$ in 250 mL MeCl was added. Two additional portions of 74.3 mL IB were added in 45 minute intervals. Forty minutes after the final addition, the flask was removed from the dry box, its contents were transferred to a 4 L beaker in the hood, and the polymerization was quenched by cautious, dropwise addition of methanol (let stir overnight). The resulting precipitated polymer was diluted to 5-10 wt percent with hexane, the solution was washed several times with water, and then dried over $MgSO_4$ overnight. This solution was gravity-filtered twice, dried, and the clear, colorless polyisobutylene, PIB, dried in a vacuum oven for several days.

Yield: 150 g (ca. 100% conversion). $M_n$ (GPC)=6500 g/mole.

Functionalization Reactions

Dehydrohalogenation

Preparation of 6K PIB—$(=CH_2)_3$

In a 2-L round-bottom flask was placed a solution of 150 g (0.075 mole functional groups) PIB—$Cl_3'$ in 1500 mL dry THF, and 42 g (0.375 mole) of potassium tert-butoxide were added. The charge was refluxed under $N_2$ for 24 hours. After cooling to room temperature, nearly all the solvent was removed by rotary evaporation and 1500 mL hexane were added. The solution was washed once with water, once with cold 5% aqueous acetic solution, and several times with water until the washings were neutral. The organic layer was dried over $MgSO_4$ overnight, the solution gravity-filtered, and the solvent removed by rotary evaporator. The product was dried in a vacuum oven at room temperature for several days.

Hydroboration/oxidation

Preparation of 6K PIB—$(OH)_3$

To a $N_2$-flushed, 1-L round-bottom flask was added a solution of 150 g olefin-ended PIB (dehydrohalogenation product, 0.075 mole olefin groups), in 200 mL dry THF. To this solution 600 mL (0.3 mole) of 9-borabicyclo[3.3.1]nonane solution (9-BBN, 0.5M in THF) were added dropwise, having been transferred to the dropping funnel under $N_2$ by a syringe. The charge was stirred at room temperature for 24 hours. The reaction mixture was then transferred to a 5-L round-bottom flask fitted with a mechanical stirrer, dropping funnel and reflux condenser, and diluted to 3-5% wt percent PIB by addition of ca. 3 L of THF. For the oxidation stage, the reagents were added in half portions due to the large scale of the charge and expected exothermicity of the reaction. A saturated methanolic solution of 18 g (0.45 mole) KOH (85 wt percent pellets) was rapidly added to the flask. 500 mL (4.2 mole) of 30% aqueous $H_2O_2$ solution were added dropwise, at a rate that would maintain a reaction temperature of 35°-40° C. Upon completion, a second portion of saturated methanolic solution of 18 g (0.45 mole) KOH was added dropwise to the flask, followed by dropwise addition of a second portion of 500 mL (4.2 mole) of 30% $H_2O_2$ solution at a rate which would maintain a temperature of 35°-40° C. The reaction mixture was heated at 40° C. for two days. The room temperature mixture was then transferred to a large separatory funnel, and 2 L of hexane were added. The mixture was washed with water until neutral, washed twice with $CH_3OH$, and washed finally with distilled water to remove the $CH_3OH$. The organic layer was dried over $MgSO_4$, gravity-filtered, and the solvent removed by a rotary evaporator. Vacuum drying at room temperature for several days afforded 142 g (94.7%) of the product.

Esterification

Preparation of 6K PIB—$(MA)_3$

To a 500 mL three-neck round-bottom flask fitted with a dropping funnel, $N_2$ inlet, and magnetic stirrer were added 9.53 g (0.00435 mole functional groups) PIB—$(OH)_3$ dissolved in 200 mL $CH_2Cl_2$. Approximately 25 mL $CHCl_3$ were then added, along with 15 mL (10.89 g, 0.108 mole) triethylamine, and the flask was placed in an ice/$H_2O$ bath. A solution of 5 mL (5.35 g, 0.051 mole) methacryloyl chloride in 80 mL $CH_2Cl_2$ was then added dropwise over a 45 minute period. Upon complete addition, the clear, yellow-gold solution was stirred for 24 hours. The solution was evaporated by a rotary evaporator, and 200 mL of hexane were added. The mixture was washed once with $H_2O$, once with cold 5% aqueous acetic acid, and several times with distilled $H_2O$ until neutral. The resulting organic layer was dried over $MgSO_4$ overnight, and gravity-filtered twice. One small hydroquinone crystal was added, and the solution was evaporated to dryness by a rotary evaporator. After drying several days under vacuum at room temperature, 9.0 g (94%) of clear, colorless tris($\omega$-methacryloyl)PIB, (PIB—(MA)$_3$), was obtained.

Synthesis of PMMA-Linked by PIB (PMMA-1-PIB) Semi-Simultaneous Interpenetrating Networks (Semi-SINs): Copolymerization of Tris($\omega$-methacryloyl)PIB with Methyl Methacrylate The procedures for solution copolymerization of PIB—(MA)$_3$ with MMA and the two-stage cure are described in the following. The scale of the charge was chosen to provide 5.5"×3.5" sheets of approximately 0.04" (1 mm) thickness of final PMMA-1-PIB semi-SIN from which test specimens could be machined. To a 100 mL round-bottom flask equipped with a magnetic stirrer were placed in order: the calculated amounts of PIB—(MA)$_3$, 40 mL THF, MMA, and AIBN. The initiator concentration was 0.5 mole percent, and the wt. percent monomers in solution was 27%. The system was thoroughly flushed with $N_2$ and heated to 60° C. by means of a silicone oil bath. The viscosity was observed visually, and the reaction continued until the onset of gelation (evidence of small amounts of gel in the charge). The times ranged from 5-8 hours for charges containing the lowest molecular weight PIB—(MA)$_3$, (6K series), to 16-20 hours for those containing the highest molecular weight PIB—(MA)$_3$, (37K series). At this point, the heating was discontinued, and the sealed flask transferred into a $N_2$-flushed inert atmosphere bag containing a rectangular Teflon cavity mold (5.5"×3.5"×0.5"). The contents of the flask were poured into the mold, the mold was sealed with a Teflon-coated rubber lid, and the assembly was removed from the bag and clamped in a press. The press was heated to 55° C. for 72 hours in a controlled temperature curing oven. Subsequently, the assembly was cooled to room temperature; the molds were removed and covered with aluminum foil, and the casts were allowed to dry slowly over two days. The foil was then perforated, and the castings were dried for an additional three days. The plates were removed from the molds, and slowly heated to 70° C. in a vacuum oven over two days, and maintained at 70° C. for five days. In this manner, rectangular plates of PMMA-1-PIB suitable for machining tensile test pieces could be prepared.

Products thus obtained can be ground into a powder, for example, having a particle size of 0.1-0.3 mm, or finer, and serve as the powder component employed with methyl methacrylate and a suitable polymerization catalyst, for example, benzoyl peroxide, in preparing the bone cements described in the preceding.

While in accordance with the patent statutes, a preferred embodiment and best mode has been presented, the scope of the invention is not limited thereto, but rather is measured by the scope of the attached claims.

What is claimed is:

1. A polymeric composition comprising poly(methyl methacrylate) cross-linked with a telechelic compound having a number average molecular weight from about 6,000 to about 25,000, and a maximum molecular weight distribution of about 1.5, selected from the group consisting of tris($\omega$-acryloyl) polyisobutylene and tris($\omega$-methacryloyl) polyisobutylene.

2. A polymeric composition according to claim 1 wherein said telechelic compound is tris($\omega$-methacryloyl) polyisobutylene.

3. A polymeric composition according to claim 2 in which tris($\omega$-methacryloyl) polyisobutylene constitutes about 5 to about 30 weight percent of said composition.

4. A polymeric composition according to claim 2 in which the number average molecular weight of said tris($\omega$-methacryloyl) polyisobutylene is from about 15,000 to about 20,000.

5. A polymeric composition according to claim 4 wherein said tris($\omega$-methacryloyl) polyisobutylene comprises about 15 to about 20 weight percent of said composition.

* * * * *